US00PP33230P2

(12) United States Plant Patent
de Jong

(10) Patent No.: US PP33,230 P2
(45) Date of Patent: Jul. 6, 2021

(54) ***SYMPHORICARPOS* PLANT NAMED 'KOLMPICA'**

(50) Latin Name: ***Symphoricarpos* x *doorenbosii***
Varietal Denomination: KOLMPICA

(71) Applicant: Kolster Holding B.V., Boskoop (NL)

(72) Inventor: Jan de Jong, Heelsum (NL)

(73) Assignee: KOLSTER HOLDING B.V., Boskoop (NL)

( * ) Notice: Subject to any disclaimer, the term of this patent is extended or adjusted under 35 U.S.C. 154(b) by 0 days.

(21) Appl. No.: 16/873,117

(22) Filed: Feb. 3, 2020

(30) Foreign Application Priority Data

Dec. 4, 2019 (CA) ..... 19-10053

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

(56) References Cited

U.S. PATENT DOCUMENTS

PP13,204 P2 * 11/2002 de Jong ..... A01H 5/00 Plt./226
PP14,536 P3 * 2/2004 Arisz ..... A01H 5/00 Plt./226
PP20,931 P2 * 4/2010 De Jong ..... A01H 5/00 Plt./226

OTHER PUBLICATIONS https://issuu.com/angelatreadwell-palmer/docs/pn_magazine0617web; Jul. 9, 2017; 1 page.*

* cited by examiner

*Primary Examiner* — Kent L Bell
(74) *Attorney, Agent, or Firm* — Penny J. Aguirre

(57) ABSTRACT

A new cultivar of *Symphoricarpos* plant named 'KOLMPICA' that is characterized by its short and compact plant habit, its strong stems and its berries that are dark pink in color.

2 Drawing Sheets

Botanical classification: *Symphoricarpos* x *doorenbosii*.
Variety denomination: 'KOLMPICA'.

CROSS-REFERENCE TO A RELATED APPLICATION

This application claims priority to a Canadian Plant Breeder's Rights Application No. 19-10053 filed on Dec. 4, 2019 under 35 U.S.C. 119(f), the entire contents of which is incorporated by reference herein.

BACKGROUND OF THE INVENTION

The present invention relates to a new and distinct cultivar of *Symphoricarpos* x *doorenbosii* that will be referred to hereafter by its cultivar name, 'KOLMPICA'. The new cultivar represents a new cultivar of snowberry or coralberry that is used as a landscape and container plant.

The new Invention arose from an ongoing controlled breeding program in Heelsum, The Netherlands. The objective was to elect a new cultivar of *Symphoricarpos* with a compact plant habit that is suitable of growing in containers. The new cultivar arose from open pollination in summer of 2004 of an unnamed and unpatented proprietary plant in the Inventor's breeding program, reference no. 02-12, as the female parent. The male parent is therefore unknown. 'KOLMPICA' was selected from amongst the resulting seedlings as a single unique plant in fall of 2007.

Asexual propagation of the new cultivar was first accomplished by the Inventor using softwood stem cuttings in winter of 2007 in Boskoop, The Netherlands. Asexual propagation by softwood stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'KOLMPICA' as a new and unique cultivar of *Symphoricarpos*.

1. 'KOLMPICA' exhibits a short and compact plant habit.
2. 'KOLMPICA' exhibits strong stems.
3. 'KOLMPICA' exhibits berries that are dark pink in color.

The female parent of 'KOLMPICA', differs from 'KOLMPICA' in having a more robust growth habit and a taller plant height. 'KOLMPICA' can be most closely compared to the *Symphoricarpos* cultivars 'Kolcharm' (U.S. Plant Pat. No. 13,204) and 'Kolmtrea' (not patented). 'Kolcharm' differs from 'KOLMPICA' in having an earlier blooming period, longer stems, and light pink berries. 'Kolmtrea' differs from 'KOLMPICA' in having a later blooming period, longer stems and darker pink berries.

BRIEF DESCRIPTION OF THE DRAWINGS

The accompanying colored photographs were taken in mid summer and illustrate the overall appearance and distinct characteristics of the new *Symphoricarpos* as grown outdoors in Boskoop, The Netherlands.

The photograph in FIG. 1 was taken of a plant 3 years in age as grown in a 5-gallon container and provides an overall view of the dense, compact habit of 'KOLMPICA' in bloom.

Figure 1:
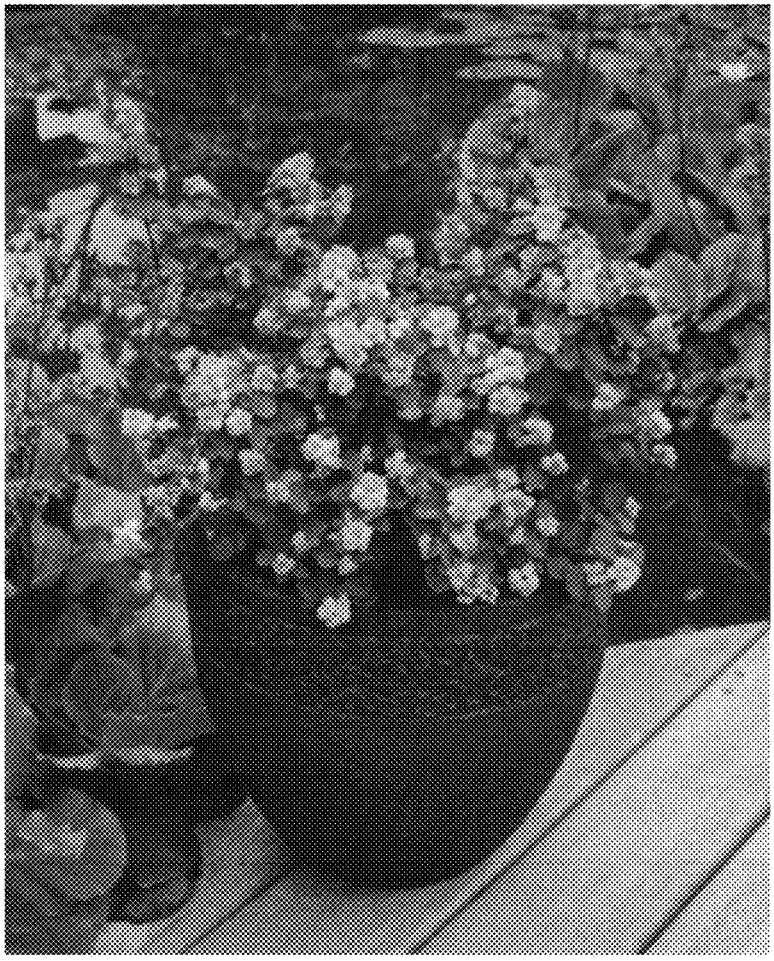
Figure 2:
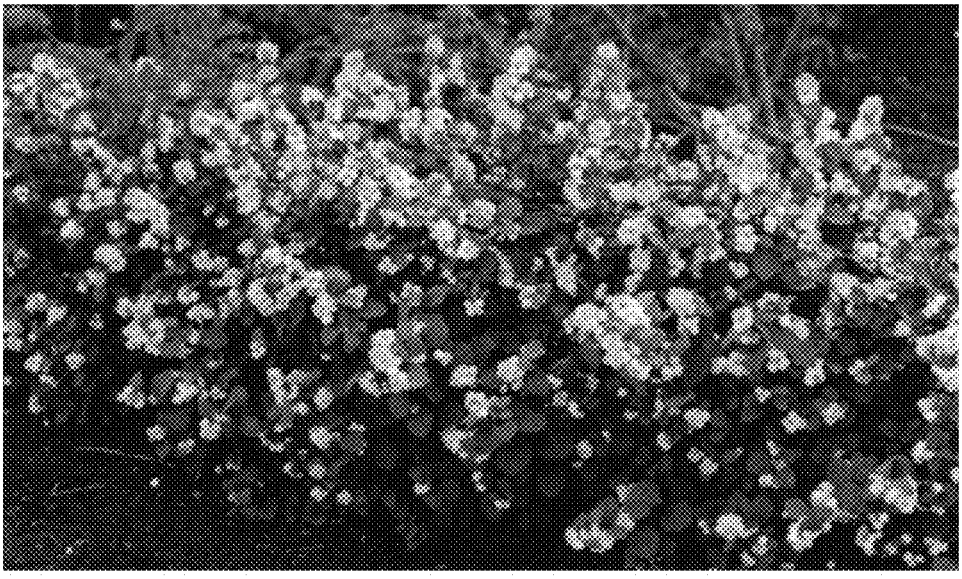

The photograph in FIG. 2 was taken of a row of 3-year-old plants of 'KOLMPICA' as grown in a trial garden.

The colors in the photographs may differ slightly from the color values cited in the detailed botanical description, which accurately describe the colors of the new *Symphoricarpos*.

DETAILED BOTANICAL DESCRIPTION

The following is a detailed description of 8-month-old plants of the new *Symphoricarpos* as grown outdoors in one-gallon containers in Richmond, Wash. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms heavily for about 4 to 5 weeks in June in The Netherlands.

*Plant habit.*—Compact mound, short stems.

*Plant size.*—Average of 55 cm in height, 45 cm in width as grown in the landscape.

*Cold hardiness.*—At least to U.S.D.A. Zone 5.

*Diseases and pests.*—Good tolerance against powdery mildew (caused by *Erysiphe diffusa* or *Microsphaera diffusa*), no susceptibility or resistance to pests has been observed.

*Root description.*—Fibrous, 161C in color.

*Propagation*—Softwood stem cuttings.

*Root development.*—Roots initiate in about 4 weeks and fully roots as young plant in about 5 months.

*Growth rate.*—Vigorous, grows 10 cm a year.

Branch description:

*Branch shape.*—Rounded.

*Stem color.*—New growth; 145A, mature wood; 151A and heavily flushed with 176A, bark 199A and N200C.

*Branch size.*—Main branches; up to 35 cm in length and 5 mm in diameter, lateral branches; an average of 26 cm in length, 2 mm in diameter.

*Branch surface.*—New growth; glabrous and glossy, mature wood is dull and smooth and becoming bark-like as it ages.

*Branching.*—Heavily branched with an average of 8 main branches, average of 12 lateral branches per main branch.

*Internode length.*—Average of 2 cm on lateral branches, 6 cm to 8 cm in main branches.

Foliage description:

*Leaf shape.*—Obtuse to elliptic.

*Leaf division.*—Simple.

*Leaf base.*—Rounded.

*Leaf apex.*—Acute.

*Leaf fragrance.*—None.

*Leaf venation.*—Pinnate, inconspicuous, colors matches leaf surface colors.

*Leaf margins.*—Entire.

*Leaf arrangement.*—Opposite and whorled down branches.

*Leaf attachment.*—Petiolate.

*Leaf surface.*—Glabrous on upper surface and lower surface.

*Leaf size.*—Average of 3 cm in length and 2 cm in width.

*Leaf quantity.*—Average of 26 pair per lateral branch.

*Leaf color.*—Young and mature upper surface; 137A, young and mature lower surface; 138A.

*Petioles.*—2 to 3 mm in length and 1.5 mm in diameter, 145A in color, glabrous surface.

*Stipules.*—None.

Flower description:

*Flower arrangement and shape.*—Single campanulate flowers arranged in terminal spikes or solitary in leaf axils; freely flowering habit with 9 to 14 flowers per spike.

*Flower aspect.*—Flowers face outwardly to drooping.

*Fragrance.*—None detected.

*Flower longevity.*—Average of 5 days, not persistent.

*Fruit longevity.*—Average of 1 month.

*Flower buds.*—Average of 2 mm in length and 1 mm in diameter, orbicular in shape, 48A and 142B in color.

*Inflorescence size.*—Average of 1.5 cm in length, 1 cm in diameter.

*Flowers.*—Average of 9 mm in length, 4 mm in diameter.

*Petals.*—5, arranged in a single whorl, slightly overlapping, petals 60% fused into base, 6 mm in length, 3 mm in width, broadly elliptic in shape, broadly acute apex, entire margins, upper surface pubescent, lower surface glabrous and smooth, color; upper and lower surface when opening and fully open 155A and 155B, flushed lightly with 68A, veins on petals also lightly flushed with 70A.

*Sepals.*—5, arranged in a single whorl, fused below the apices, average of 0.5 mm in length, 1 mm in width at the widest point, acute apex, entire margins, inner and outer surface glabrous, color; outer surface 145A, flushed with 71A, inner surface 145A.

*Calyx.*—Funnelform, 1 mm in length and diameter.

*Peduncles.*—Strong, 144B in color, up to 4 mm in length, 1 mm in width, glabrous and slightly glossy surface.

*Pedicels.*—None, sessile to peduncle.

Reproductive organs:

*Gynoecium.*—Pistils; 1, average of 3 mm in length, stigma; club-shaped, average of 0.5 mm in width, 22A in color, style; average of 2.5 mm in length, NN155C in color, ovary; average of 0.5 mm in diameter, 149A in color.

*Androecium.*—Stamens; 5, 0.5 mm in length, anthers; narrow oblong in shape, average of 1 mm in length, 22A in color, pollen; abundant in quantity, 11A in color.

*Fruits.*—Average of 1.5 cm in diameter, 1.2 cm in length, spherical in shape, smooth in texture, color; a blend of NN155C, 69A, 62A and 62B.

*Seeds.*—Average of length 3 mm, average of 2 mm in diameter, 158A in color.

It is claimed:

1. A new and distinct cultivar of *Symphoricarpos* plant named 'KOLMPICA' as herein illustrated and described.

* * * * *